(12) United States Patent
Li

(10) Patent No.: US 6,911,221 B2
(45) Date of Patent: Jun. 28, 2005

(54) ANTI-NEOPLASTIC DRUG

(76) Inventor: Hongfen Li, Room 902, 3d Entrance, No. 1 Building, Lotus Residential Quarters, Haidian District, Beijing (CN), 1000000

(*) Notice: Subject to any disclaimer, the term of this patent is extended or adjusted under 35 U.S.C. 154(b) by 0 days.

(21) Appl. No.: 10/473,023

(22) PCT Filed: Nov. 1, 2001

(86) PCT No.: PCT/CN01/01521
§ 371 (c)(1), (2), (4) Date: Jan. 29, 2004

(87) PCT Pub. No.: WO02/078722
PCT Pub. Date: Oct. 10, 2002

(65) Prior Publication Data
US 2004/0109904 A1 Jun. 10, 2004

(51) Int. Cl.⁷ ............................ A61K 35/78; A01N 65/00
(52) U.S. Cl. .................................................... 424/728
(58) Field of Search ........................................ 424/728

(56) References Cited

U.S. PATENT DOCUMENTS

| | | | |
|---|---|---|---|
| 4,613,591 A | * | 9/1986 | Aburada et al. ............... 514/34 |
| 4,618,495 A | * | 10/1986 | Okuda et al. ............... 424/728 |
| 5,437,866 A | * | 8/1995 | Sun ............................ 424/741 |

FOREIGN PATENT DOCUMENTS

| | | |
|---|---|---|
| CN | 1097621 A | 1/1995 |
| CN | 1145240 A | 3/1997 |
| CN | 1157737 A | 8/1997 |
| CN | 1205880 A | 1/1999 |

OTHER PUBLICATIONS

Traditional Chinese Medicine of GuangXi, vol. 8(1), 1985, Chen Jin. Theory of Eliminating the Evil Factors and Restorating Healthy Energy in Traditional Chinese Medicine and Research on Anticancerous Chinese Medicinal Herb:, 47–49.

* cited by examiner

Primary Examiner—Christopher R. Tate
Assistant Examiner—S. B. McCormick-Ewoldt
(74) Attorney, Agent, or Firm—Fay, Sharpe, Fagan, Minnich & McKee, LLP (57) ABSTRACT

A unique class of anti-neoplastic compositions are described. The compositions contain certain Chinese medicinal herbs: Panax ginsing, Poria cocos, Atractylodes macrocephala, Angelic sinensis, Astragalus membranaceus, Curcuma zedoaria, Scutellaria baicalensis, Coptis chinenisis, Glycyrrhiza uralenisis, Crataegus pinatifida, Hordeum vulgare, Schisandra chinensis, Hedyotis diffusa, Ophiophogon japonicus, and Lobelia chinesis lour. Extensive testing indicates an effective treatment rate of 69.7% and 84.3% when used in combination with radiotherapy or chemotherapy. The animal trials conducted demonstrate that the anti-neoplastic compositions increase the activity of NK cells, and reduce and prevent metastasis of tumors under stress conditions.

20 Claims, 1 Drawing Sheet

The effects of increasing doses of ACNO (low, medium, high: 0.1, 0.5, or 2 g/kg/day) on NK activity (%specific killing) in increasing effector to target (E/T) ratios. Data are presented as means ± S.E.M. ACNO caused a significant dose-dependent increase in NK activity without significantly affecting number of NK cells (not shown).

Fig. 1. The effects of increasing doses of ACNO (low, medium, high: 0.1, 0.5, or 2 g/kg/day) on NK activity (%specific killing) in increasing effector to target ($E/T$) ratios. Data are presented as means ± S.E.M. ACNO caused a significant dose-dependent increase in NK activity without significantly affecting number of NK cells (not shown).

Fig. 2. The effects of ACNO (2 g/kg/day) and of the $\beta$-adrenergic agonist, metaproterenol (0.8 mg/kg), on the number of MADB106 metastases. Data are presented as means ± S.E.M. Metaproterenol injection significantly increased the number of metastases, and ACNO significantly reduced this effect of metaproterenol (*) without altering baseline levels of metastasis (in saline-injected animals).

ANTI-NEOPLASTIC DRUG

FIELD OF THE INVENTION

The present invention relates to compositions for treatment of cancer and specifically, tumors. More particularly, the present invention is directed to anti-neoplastic compositions comprising a particular combination of herbs.

BACKGROUND OF THE INVENTION

According to the data released by the Ministry of Public Health of China, cancer was ranked as the number one cause of death in urban areas of China in 1990. More than one million patients die from cancer every year in mainland China. In the United States, one person dies from cancer every minute. And in the United States, there are 3 million cancer patients, one-third of which will eventually die from this disease. At present, more than 100 different types of cancer have been identified.

Although operation, radiotherapy and chemotherapy are used as the main therapeutics, it is well known that the treatment of middle and late stage cancer is very difficult. There are many patients whose cancer has progressed such that they are inoperable. Furthermore, chemotherapy and radiotherapy do not always result in the desired effect. Moreover, these treatment strategies have serious side effects, including weakness, anorexia, loss of hair, inhibition of the function of bone marrow hematopoiesis, impairment of liver and kidney and ovary function, etc. After such treatments, patients often relapse because the immune system is extremely suppressed, typically for ten hours after operation. It is therefore pertinent that a new therapeutic strategy is identified to enhance cancer treatment as well as reduce the side effects of operation, chemotherapy and radiotherapy.

Traditional Chinese medicine has been used clinically for more than 3000 years. As a result, vast clinical experience has been obtained. Chinese medicine has provided unexpected and beneficial effects in the treatment of various diseases, including cancer. However, it was not until the last three decades that modern scientific methods have been used to test traditional Chinese medicine and reveal that such medical practices often provide remarkable results.

Research and development of anti-cancer drugs from plants have been very beneficial. Advances in biochemical and pharmacological studies of plant-derived drugs have resulted in significant impetus on the further research and development of anti-cancer drugs from plants. However, currently available medicines only emphasize a single aspect of cancer treatment, for example, only for increasing the function of the immune system, or only for suppressing tumors, or only for improving blood circulation, etc.

Accordingly, there is a need for an improved formulation and methodology for treating cancer, and specifically for tumors.

SUMMARY OF THE INVENTION

The objective of the present invention is to provide new anti-cancer compositions that are believed to strengthen the body's resistance and thereby eliminate pathogenic factors. These compositions are believed to increase the function of the immune system, and impart anti-stress and anti-tumor characteristics to the body. The compositions are further believed to improve micro-circulation and thereby reverse and destroy tumor cells. The clinical trials described herein demonstrate that the new anti-neoplastic compositions of the present discovery possess significant therapeutic efficacy.

DETAILED DESCRIPTION OF THE PREFERRED EMBODIMENTS

The various compositions for treatment of cancer and tumors specifically comprise one or more, or all, of the following Chinese herbal medicines: Red Ginseng (also known as Red Ren Shen) (*PANAX GINSING*), Fu Ling (*PORIA COCOS*), Bai Zhu (*ATRACTYLODES MACROCEPHALA*), Dang Gui (*ANGELIC SINENSIS*), Huang Qi (*ASTRAGALUS MEMBRANACEUS*), E Zhu (*CURCUMA ZEDOARIA*), Huang Qin (*SCUTELLARIA BAICALENSIS*), Huang Lian (*COPTIS CHINENSIS*), Huang Bai (*PHELLODRON CHINENSE*), Gan Cao (*GLYCYRRHIZA URALENSIS*), Shan Zha (*CRATAEGUS PINATIFIDA*), Mai Ya (*HORDEUM VULGARE*), Dan Shen (*SALVIA MILTIORRHIZA*), Wu Wei Zi (*SCHISANDRA CHINENSIS*), Bai Hua She She Cao (*HEDYOTIS DIFFUSA*), Mai Men Dong (*OPHIOPHOGON JAPONICUS*), Ban Bian Lian (*LOBELIA CHINESIS LOUR*), Ban Zhi Lian (*SCUTELLARIA BARBABA*), Shen Qu (*MASSA FERMENTATA MEDICALIS*), Chai Hu (*BUPLEURUM SCORZONERIFOLIUM*), Ban Xia (*PINELLIA TERNATA*), Chen Pi (*CITRUS RETICULATA*), Chuan Lian Zi (*MELIA TOOSENDAN*), Bai Shao (*PAEONIA LACTIFLORA*), Ling Zhi (*GANODERMA LUCIDUM*), and Jiang (dry or fresh) (*ZINGIBER OFFICINALE*).

More specifically, the preferred compositions comprise Red Ginseng (*PANAX GINSING*), Fu Ling (*PORIA COCOS*), Bai Zhu (*ATRACTYLODES MACROCEPHALA*), Huang Qi (*ASTRAGALUS MEMBRANACEUS*), Huang Qin (*SCUTELLARIA BAICALENSIS*), Huang Lian (*COPTIS CHINENSIS*), Gan Cao (*GLYCYRRHIZA URALENSIS*), Mai Ya (*HORDEUM VULGARE*), Bai Hua She She Cao (*HEDYOTIS DIFFUSA*), Ban Bian Lian (*LOBELIA CHINESIS LOUR*), Ban Zhi Lian (*SCUTELLARIA BARBABA*), Shen Qu (*MASSA FERMENTATA MEDICALIS*), and one or more of the following: Dang Gui (*ANGELIC SINENSIS*), E Zhu (*CURCUMA ZEDOARIA*), Huang Bai (*PHELLODRON CHINENSE*), Shan Zha (*CRATAEGUS PINATIFIDA*), Dan Shen (*SALVIA MILTIORRHIZA*), Wu Wei Zi (*SCHISANDRA CHINENSIS*), Mai Men Dong (*OPHIOPHOGON JAPONICUS*), Chai Hu (*BUPLEURUM SCORZONERIFOLIUM*), Ban Xia (*PINELLIA TERNATA*), Chen Pi (*CITRUS RETICULATA*), Chuan Lian Zi (*MELIA TOOSENDAN*), Bai Shao (*PAEONIA LACTIFLORA*), Ling Zhi (*GANODERMA LUCIDUM*), and Jiang (dry or fresh) (*ZINGIBER OFFICINALE*).

The following specific prescriptions are the most preferred compositions. Prescription 1 is a primary or basic composition and Prescriptions 2 to 6 are adding or reducing compositions. Additional aspects of these compositions and their use are described in greater detail herein.

PRESCRIPTION 1

| Name (pinyin) | Latin Name (species) | % amount (w/w) |
|---|---|---|
| Red Ren Shen | PANAX GINSING | 9.4% |
| Fu Ling | PORIA COCOS | 5.7% |
| Bai Zhu | ATRACTYLODES MACROCEPHALA | 5.7% |
| Dang Gui | ANGELIC SINENSIS | 6.6% |
| Huang Qi | ASTRAGALUS MEMBRANACEUS | 5.7% |
| E Zhu | CURCUMA ZEDOARIA | 4.7% |
| Huang Qin | SCUTELLARIA BAICALENSIS | 5.7% |
| Huang Bai | PHELLODRON CHINENSE | 4.7% |
| Huang Lian | COPTIS CHINENSIS | 5.7% |
| Gan Cao | GLYCYRRHIZA URALENSIS | 5.7% |
| Shan Zha | CRATAEGUS PINATIFIDA | 4.7% |
| Mai Ya | HORDEUM VULGARE | 1.8% |
| Dan Shen | SALVIA MILTIORRHIZA | 4.7% |
| Wu Wei Zi | SCHISANDRA CHINENSIS | 5.7% |
| Bai Hua She She Cao | HEDYOTIS DIFFUSA | 6.6% |
| Mai Men Dong | OPHIOPHOGON JAPONICUS | 4.7% |
| Ban Bian Lian | LOBELIA CHINESIS LOUR | 4.7% |
| Ban Zhi Lian | SCUTELLARIA BARBABA | 5.7% |
| Shen Qu | MASSA FERMENTATA MEDICALIS | 1.8% |

PRESCRIPTION 2

| Name (pinyin) | Latin Name (species) | % amount (w/w) |
|---|---|---|
| Red Ren Shen | PANAX GINSING | 9.4 (1–15)% |
| Fu Ling | PORIA COCOS | 5.7 (1–10)% |
| Bai Zhu | ATRACTYLODES MACROCEPHALA | 5.7 (1–10)% |
| Dang Gui | ANGELIC SINENSIS | 6.6 (1–10)% |
| Huang Qi | ASTRAGALUS MEMBRANACEUS | 5.7 (1–10)% |
| E Zhu | CURCUMA ZEDOARIA | 4.7 (1–10)% |
| Huang Qin | SCUTELLARIA BAICALENSIS | 5.7 (1–25)% |
| Huang Bai | PHELLODRON CHINENSE | 4.7 (1–20)% |
| Huang Lian | COPTIS CHINENSIS | 5.7 (1–20)% |
| Gan Cao | GLYCYRRHIZA URALENSIS | 5.7 (1–15)% |
| Shan Zha | CRATAEGUS PINATIFIDA | 4.7 (1–10)% |
| Mai Ya | HORDEUM VULGARE | 1.8 (1–20)% |
| Dan Shen | SALVIA MILTIORRHIZA | 4.7 (1–15)% |
| Wu Wei Zi | SCHISANDRA CHINENSIS | 5.7 (1–15)% |
| Bai Hua She She Cao | HEDYOTIS DIFFUSA | 6.6 (1–40)% |
| Mai Men Dong | OPHIOPHOGON JAPONICUS | 4.7 (1–20)% |
| Ban Bian Lian | LOBELIA CHINESIS LOUR | 4.7 (1–25)% |
| Ban Zhi Lian | SCUTELLARIA BARBABA | 5.7 (1–25)% |
| Shen Qu | MASSA FERMENTATA MEDICALIS | 1.8 (1–20)% |

PRESCRIPTION 3

| Name (pinyin) | Latin Name (species) | % amount (w/w) |
|---|---|---|
| Red Ren Shen | PANAX GINSING | 9.4(1–30)% |
| Fu Ling | PORIA COCOS | 5.7(1–30)% |
| Bai Zhu | ATRACTYLODES MACROCEPHALA | 5.7(1–30)% |
| Dang Gui | ANGELIC SINENSIS | 6.6(1–30)% |
| Huang Qi | ASTRAGALUS MEMBRANACEUS | 5.7(1–30)% |
| E Zhu | CURCUMA ZEDOARIA | 4.7(1–30)% |
| Huang Qin | SCUTELLARIA BAICALENSIS | 5.7(1–35)% |
| Huang Bai | PHELLODRON CHINENSE | 4.7(1–30)% |
| Huang Lian | COPTIS CHINENSIS | 5.7(1–30)% |
| Gan Cao | GLYCYRRHIZA URALENSIS | 5.7(1–30)% |
| Shan Zha | CRATAEGUS PINATIFIDA | 4.7(1–30)% |
| Mai Ya | HORDEUM VULGARE | 1.8(1–30)% |
| Dan Shen | SALVIA MILTIORRHIZA | 4.7(1–30)% |
| Wu Wei Zi | SCHISANDRA CHINENSIS | 5.7(1–30)% |
| Bai Hua She She Cao | HEDYOTIS DIFFUSA | 6.6(1–40)% |
| Mai Men Dong | OPHIOPHOGON JAPONICUS | 4.7(1–30)% |
| Ban Bian Lian | LOBELIA CHINESIS LOUR | 4.7(1–35)% |
| Ban Zhi Lian | SCUTELLARIA BARBABA | 5.7(1–35)% |
| Shen Qu | MASSA FERMENTATA MEDICALIS | 1.8(1–30)% |

PRESCRIPTION 4

| Name (pinyin) | Latin Name (species) | % amount (w/w) |
|---|---|---|
| Red Ren Shen | PANAX GINSING | 9.4 (1–30)% |
| Fu Ling | PORIA COCOS | 5.7 (1–30)% |
| Bai Zhu | ATRACTYLODES MACROCEPHALA | 5.7 (1–30)% |
| Dang Gui | ANGELIC SINENSIS | 6.6 (1–30)% |
| Huang Qi | ASTRAGALUS MEMBRANACEUS | 5.7 (1–30)% |
| Huang Qin | SCUTELLARIA BAICALENSIS | 5.7 (1–30)% |
| Huang Lian | COPTIS CHINENSIS | 5.7 (1–30)% |
| Huang Bai | PHELLODRON CHINENSE | 4.7 (1–30)% |
| Gan Cao | GLYCYRRHIZA URALENSIS | 5.7 (1–30)% |
| Mai Ya | HORDEUM VULGARE | 1.8 (1–30)% |
| Bai Hua She She Cao | HEDYOTIS DIFFUSA | 6.6 (1–40)% |
| Ban Bian Lian | LOBELIA CHINESIS LOUR | 4.7 (1–30)% |
| Ban Zhi Lian | SCUTELLARIA BARBABA | 5.7 (1–30)% |
| Shen Qu | MASSA FERMENTATA MEDICALIS | 1.8 (1–30)% |
| Chai Hu | BUPLEURUM SCORZONERIFOLIUM | 5 (1–30)% |
| Ban Xia | PINELLIA TERNATA | 5 (1–30)% |
| Chen Pi | CITRUS RETICULATA | 5 (1–30)% |
| Chuan Lian Zi | MELIA TOOSENDAN | 5 (1–30)% |
| Bai Shao | PAEONIA LACTIFLORA | 4 (1–30)% |
| Jiang(GAN or SHENG) | ZINGIBER OFFICINALE(dry or fresh) | 2 (1–30)% |

PRESCRIPTION 5

| Name (pinyin) | Latin Name (species) | % amount (w/w) |
|---|---|---|
| Red Ren Shen | PANAX GINSING | 9.4 (1–30)% |
| Fu Ling | PORIA COCOS | 5.7 (1–30)% |
| Bai Zhu | ATRACTYLODES MACROCEPHALA | 5.7 (1–30)% |
| Dang Gui | ANGELIC SINENSIS | 6.6 (1–30)% |
| Huang Qi | ASTRAGALUS MEMBRANACEUS | 5.7 (1–30)% |
| Huang Qin | SCUTELLARIA BAICALENSIS | 5.7 (1–30)% |
| Huang Lian | COPTIS CHINENSIS | 5.7 (1–30)% |
| Huang Bai | PHELLODRON CHINENSE | 4.7 (1–30)% |
| Gan Cao | GLYCYRRHIZA URALENSIS | 5.7 (1–30)% |
| Mai Ya | HORDEUM VULGARE | 1.8 (1–30)% |
| Ban Bian Lian | LOBELIA CHINESIS LOUR | 4.7 (1–30)% |
| Bai Hua She She Cao | HEDYOTIS DIFFUSA | 6.6 (1–40)% |
| Ban Zhi Lian | SCUTELLARIA BARBABA | 5.7 (1–30)% |
| Shen Qu | MASSA FERMENTATA MEDICALIS | 1.8 (1–30)% |
| Chai Hu | BUPLEURUM SCORZONERIFOLIUM | 5 (1–20)% |
| Ban Xia | PINELLIA TERNATA | 5 (1–30)% |
| Chen Pi | CITRUS RETICULATA | 5 (1–30)% |
| Chuan Lian Zi | MELIA TOOSENDAN | 5 (1–30)% |
| Bai Shao | PAEONIA LACTIFLORA | 4 (1–30)% |

In prescription 5, 2 (1–30) % of JIANG (GAN or SHENG) (*ZINGIBER OFFICINALE*) (dry or fresh) can be added, or 4.7 (1–30) % of Huang Bai (*PHELLODRON CHINENSE*) can be cancelled.

PRESCRIPTION 6

| Name (pinyin) | Latin Name (species) | % amount (w/w) |
|---|---|---|
| Red Ren Shen | PANAX GINSING | 9.4 (1–30)% |
| Fu Ling | PORIA COCOS | 5.7 (1–30)% |
| Bai Zhu | ATRACTYLODES MACROCEPHALA | 5.7 (1–30)% |
| Dang Gui | ANGELIC SINENSIS | 6.6 (1–30)% |
| Huang Qi | ASTRAGALUS MEMBRANACEUS | 5.7 (1–30)% |
| Huang Qin | SCUTELLARIA BAICALENSIS | 5.7 (1–30)% |
| Huang Lian | COPTIS CHINENSIS | 5.7 (1–30)% |
| Huang Bai | PHELLODRON CHINENSE | 4.7 (1–30)% |
| Gan Cao | GLYCYRRHIZA URALENSIS | 5.7 (1–30)% |
| Mai Ya | HORDEUM VULGARE | 1.8 (1–30)% |
| Ban Bian Lian | LOBELIA CHINESIS LOUR | 4.7 (1–30)% |
| Bai Hua She She Cao | HEDYOTIS DIFFUSA | 6.6 (1–40)% |
| Ban Zhi Lian | SCUTELLARIA BARBABA | 5.7 (1–30)% |
| Shen Qu | MASSA FERMENTATA MEDICALIS | 1.8 (1–30)% |
| Chai Hu | BUPLEURUM SCORZONERIFOLIUM | 5 (1–30)% |
| Ban Xia | PINELLIA TERNATA | 5 (1–30)% |
| Chen Pi | CITRUS RETICULATA | 5 (1–30)% |
| Chuan Lian Zi | MELIA TOOSENDAN | 5 (1–30)% |
| Bai Shao | PAEONIA LACTIFLORA | 4 (1–30)% |
| Ling Zhi | GANODERMA LUCIDUM | 6 (1–30%) |

In prescription 6, 2 (1–30)% of Jiang (GAN or SHENG) (*ZINGIBER OFFICINALE*) (dry or fresh) can be added, or 4.7 (1–30)% of Huang Bai (*PHELLODRON CHINENSE*) can be cancelled.

In each above mentioned prescriptions, the numbers shown in parenthesis represent that the percentage amount can vary within the range. The number shown immediately before the parenthesis is the preferred concentration. For example, in Prescription 6, Ling Zhi is preferably used in a concentration of 6%, however it may be used in a concentration of 1–30%. Furthermore, it will be appreciated that all percentages are approximate.

The new anti-neoplastic compositions of the present invention are designated herein as Anti-Cancer Number One (hereinafter referred to as simply ACNO). These compositions provide new anti-cancer drugs and treatment regimes based upon traditional Chinese medicines and practices. The prescriptions are based upon Si Junzi Tang (Decoction of Four Noble Drugs) and Huanglian Jiedu Tang (Antidotal Decoction of coptis), and are formulated by adding therein drugs or agents for replenishing Qi and blood, and including other agents for detoxifying and providing an anti-tumor function. The function of Si Junzi Tang is to replenish Qi and strengthen the spleen. Among the four ingredients in the prescription, Ginseng is sweet in flavor and warm in nature, and possesses the effect of invigorating primordial Qi and acts as a principal drug to strengthen the spleen and nourish the stomach. Bai Zhu has a bitter flavor and warm nature and is effective for strengthening the spleen and eliminating dampness and is considered as an assistant drug. Fu Ling, being sweet and insipid in flavor, serves as an adjuvant drug in achieving the effect of strengthening the spleen. Gan Cao, being sweet in flavor and warm in nature, is used as a guiding drug for regulating the meddle-warmer. In the Huanglian Jiedu Tang, ingredient Huang Lian is used as principal drug, which plays a significant role of purging pathogenic fire in the heart and middle-energizer. Huang Qin acts as an assistant drug with the effect of clearing away heat in the lung and purging fire in the upper-energizer. Huang Bai is used as both adjuvant and guiding drugs, the former provides the effect of purging pathogenic fire in lower-energizer and the latter have the effect of removing pathogenic fire in the tri-energizer by inducing diuresis.

In the prescriptions of the present invention, Ginseng, Huang Qi, Bai Zhu, Gan Cao, which are sweet in flavor and warm in nature, are able to strengthen the spleen and invigorate the Qi. Dang Gui, which is sweet and pungent in flavor and warm in property, can play the role of tonifying the blood and nourishing the liver. E Zhu relieves the stagnation of Qi, alleviates pain and invigorates blood circulation. Dan Shen can invigorate blood circulation, remove blood stasis, remove heat from blood, treat carbuncles, and tranquilizes the disturbed mind by nourishing the blood. Wu Wei Zi nourishes the kidney and tranquilizes the mind. Mai Man Dong nourishes yin, promotes the production of body liquid and clears away heat-fire to relieve vexation, which combines with Ren Shen for treating the injury of Qi and Yin by heat, palpitation and pulse insufficiency of the patient after chemotherapy. Bai Hua She She Cao, Bai Zhi Lian, and Ban Bian Lian assist Huang Lian Jie Du Tang with clearing heat and detoxifying to fight against tumors. Shan Zha, Mai ya, and Shen Qu strengthen the spleen and improve digestion in order to prevent the drugs for replenishing Qi and blood (Yi Qi Bu Xue Yao) from growing and loathing Qi to block the spleen and the stomach's function of transport and digestion. The action of the whole formula is tonifying but not stagnant, and is purgation but not asthenia. So, the formula increases an organism's immunity function and inhibits/kills the tumor at the same time. Therefore, the prescriptions of the present invention are developed according to a theory of strengthening a body's resistance to eliminate pathogenic factors of traditional Chinese medicine. Furthermore, the various prescriptions are based upon a theory of increasing the function of the immune system, improving anti-stress and anti-tumor characteristics and further improving micro-circulation to reverse and destroy tumor cells of Western medicine.

Extensive clinical testing of ACNO has revealed that the use of ACNO for treating patients with cancer leads to excellent clinical efficacy results. Effective treatment rates of 69.7% have been obtained. When administered in combination with radiotherapy or chemotherapy, effective treatment rates of 84.3% have been obtained.

Distinguished from Western medicine, the main principles of cancer treatment in anti-cancer number one (ACNO) are: searching for the primary cause of disease in treatment, and treating the physical and mental aspects as a whole instead of paying attention to the local target lesion only. This therapeutic method was easy, effective, and safe without any adverse effect, which renders it suitable for the elderly and asthenics, who are unable or who have failed to receive an operation, chemotherapy and/or radiotherapy. It has been demonstrated by clinical practice that ACNO inhibits/kills cancer cells (eliminating pathogenic factors); enhances the immune function of the organism, increases NK cells' activity; possesses the function of anti-stress and improves micro-circulation and suppresses the genesis and metastasis of tumor; increases sensitivity to other therapies and diminishes toxic and adverse action of other therapies and drugs. So, ACNO enhances the body's anti-tumor capacity, improves the patient's quality of life and reduces or prevents the genesis, relapse and metastasis of tumors. For further proving the therapeutic efficacy of ACNO, animal trials were conducted at the Tel-Aviv University of Israel to test the effects of ACNO on natural killer cell activity and metastasis of tumors.

Research Efforts in Animals
Experiments and Materials
1. Fischer-344 male and female rats (Harlan Laboratories of Jerusalem, Israel) were housed four in a cage with free access to food and water ad libitum in a 12:12 hours lighting regiment. Animals were acclimatized to the surrounding for at least 3 weeks before any experiment, and were weighed three times. All experiments were conducted during the first half of the light phase. In each experiment, all animals were of the same age.

2. ACNO was prepared in China, and contained Red Ginseng, *Atractylodes Macrocephala, Poria Cocos*, etc. The ACNO composition was as described herein.

3. The experimental animals were divided into a test group and a control group. The animals in the test group were fed with 0.1, 0.5, 2 g/kg body weight ACNO mixed and standard powdered rodent food to which water was added (test food), every day. The animals in the control group received the same wet food mixture without ACNO (control food) in the same amount. All animals were fed at regular times every day. To adjust animals to the feeding protocol, all rats received the wet mixture without ACNO for 3 days before each experiment. Thereafter, the animals were fed test food and control food, respectively. Rats from all groups consumed more than 95% of the food each day. Approximately 70% of it was consumed during the dark phase. Body weight of each animal was monitored twice a week during the experiment.

4. MADB106 tumor cell—MADB106 cell was obtained from a pulmonary metastasis of a mammary adenocarcinoma (MADB100) by a special incubation.

5. Induction and counting of tumor metastasis—Rats were lightly anesthetized with halothane, and then $10^5$ MADB106 tumor cells were injected into their tail vein. At the same time, number 3 and 4 of the animals in every group were injected with 0.8 ml β-receptor agonist Metaproterenol MP. Rats were anesthetized with halothane after they were fed with ACNO for 3 weeks counted from the day of tumor inoculation, and their lungs were removed and placed in Bouin solution (72% saturated picric acid solution, 23% formaldehyde [37% solution] and 5% glacial acetic acid) for 24 h. Thereafter, the lungs were washed with ethanol, and then the cell number of pulmonary metastasis were counted by two experimenters unaware of the group origin (in a blind technique), independently. The obtained data were analyzed statistically.

6. After the animals had been fed with the test food for 2 weeks, 1 ml of blood was drawn by cardiac puncture to detect the number of NK cells per ml and the activity thereof.

Statistical Analysis
ANOVA method was applied for detecting the number of NK cells per ml and the activity thereof, while a T test and the ANOVA test were used for the count of the cell number of pulmonary tumors.

Experimental Method
1. The Effect of ACNO on Number and Activity of NK Cells

78% healthy female Fisher rats that were 10–12 weeks old and of 250–350 g body weight, were randomly divided into 5 groups, wherein 3 groups were administrated ACNO with high, middle and low dosage (0.1, 0.5, 2.0 g/kg body weight/day). There were 14, 15, 14, 15 and 20 rats in a low, a middle, and a high dosage groups, a *Panax ginsing* group (0.5 g *Panax Ginsing*/kg body weight/day) and a control group (fed with the control food in same amount only), respectively. Two weeks after administration, rats were lightly anesthetized with halothane, blood samples were drawn by cardiac puncture and placed into a tube with heparin, and centrifuged to collect monocytes. The monocytes were washed with PBS twice, and the concentration of the cells were adjusted to $0.25 \times 10^7$. Thereafter, the number of NK cells were counted, and the activity of NK cells was detected by the method using YAC-1 or MADB106 target cells by releasing $^{51}Cr$ or $^{125}IDUR$.

2. The Effect of ACNO on Susceptibility to Tumor Cells Metastasis 89 healthy female Fischer rats that were 7–8 weeks old and of 120–170 g body weight (48 females and 61 males), were randomly divided into 2 groups, an experiment group and a control group. There were 40 rats (20 females and 20 males) and 49 rats (20 females and 29 males) in the experiment group and the control group, respectively. The animals in the experiment group were fed with 2 g/kg body weight/day ACNO and water-added mix food while those in the control group were fed with water-added mix food in same amount. After 3 weeks of feeding, rats were lightly anesthetized with halothane, and then 0.5 ml of $4 \times 10^5$ tumor cells were injected into their tail vein. At the same time, 0.8 ml, β-receptor agonist (MP) were injected. Three weeks after inoculating tumor cells, rats were anesthetized with halothane, and then their lungs were removed and fixed in Bouin solution for 24 h. Thereafter, the lungs were washed with ethanol, and then the cell number of pulmonary metastasis were counted by two experimenters unaware of the group origin (in a blind technique), independently. The obtained data were analyzed statistically.

Results
1. The Effect of ACNO on NK Cells

Rats from all groups consumed 95% of their food each day, and during the experimental period, gained an average of 23.4 g/week in body weight with no significant difference among various groups.

Figure 1:
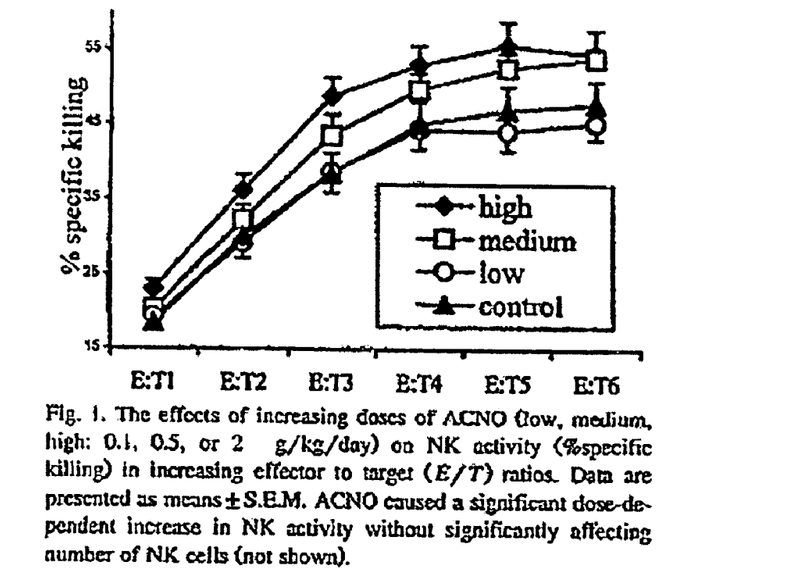
FIG. 1 shows the effects of increasing doses of ACNO (low, medium and high: 0.1, 0.5 and 2 g/kg/day) on NK activity (% specific killing) in increasing effector to target (E/T) ratios. ACNO caused a significant dose-dependent increase in NK activity ($P<0.0001$).

The results showed that ACNO caused a significant dose-dependent increase in activity of NK cells per ml blood. FIG. 1 illustrates the specific percentages of different E:T rates in various groups. Compared to the animals in the control group, those in the high dose group showed a significantly higher activity of NK cells ($P<0.0001$), and the other administration groups also showed increased activity of NK cells to a different degree without significant difference. This result suggested that the effect of a high dose was superior to that of a low dose. On the other hand, ACNO also caused an increased number of NK cells/ml blood, wherein the number value of NK cells/ml blood in the control group is 344.4±34.9 (mean±SD), that in the high dose group is 530±79.1 (mean±SD), that in the medium dose group is 407.7±63.6 (mean±SD), that in the low dose group is 382.2±53.2 (mean±SD), and that in the Panax Ginsing group is 373±65.1 (mean±SD). This result demonstrated that ACNO increased significantly the activity and number of NK cells.

Figure 2:
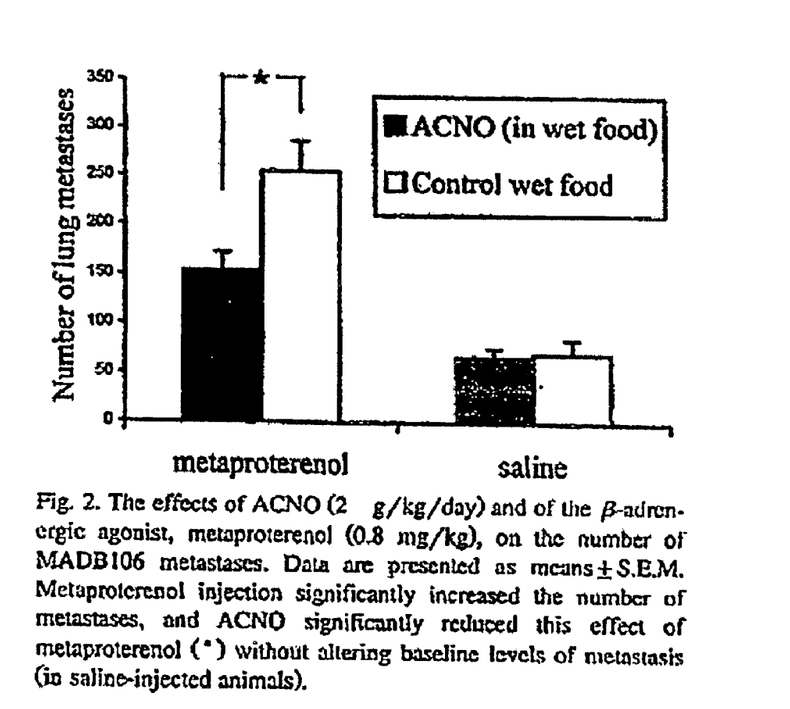
FIG. 2 shows the effects of ACNO (2 g/kg/day) and of $\beta$-receptor agonist (MP) (0.8 g/kg body weight) on the cells number of MADB 106 metastases, wherein MP injection significantly increased the cells number of metastases, while ACNO administration significantly decreased the cells number of metastases ($P<0.0006$).

Specifically, FIG. 1 illustrates the effects of increasing doses of ACNO (low, medium, high: 0.1, 0.5, or 2 g/kg/day) on NK activity (% specific killing) in increasing effector to target (E/T) ratios. Data are presented as means±S.E.M. ACNO caused a significant dose dependent increase in NK activity without significantly affecting the number of NK cells (not shown). FIG. 2 shows the effects of ACNO (2 g/kg/day) and of the β-adrenergic agonist, metaproterenol (0.8 mg/kg), on the number of MADB106 metastases. Data are presented as means±S.E.M. Metaproterenol injection significantly increased the number of metastases, and ACNO significantly reduced this effect of metaproterenol (*) without altering baseline levels of metastasis (in saline-injected animals).

2. The Effect of ACNO on Tumor Cells Metastasis

During the experimental period, rats from the two groups consumed 95% of their food, and gained an average of 20.5 g/week (males) or log/week (females) in body weight, with no significant difference as compared to the third group maintained on ad libitum dry food schedule.

With respect to cell number of metastasis, the difference between those counted by the two experimenters was lower than 0.9, and the average thereof was used. There is no significant difference among the three groups (dry food, wet food only, and ACNO group) without the administration of β-receptor agonist. However, compared to the 2 control groups without the administration of β-receptor agonist, the 2 control groups with the administration of β-receptor agonist, caused a 4 to 5.5 fold increase in the cell number of metastases (NS70+14, MP255+32), while ACNO-treated groups only caused a 2.3 fold increase (ACNO+MP154+18, control group+MP255+32), $P<0.0006$. This experimental result showed that the state of stress and anxiety significantly promoted the tumor metastases, however, ACNO remarkably inhibited the tumor metastases under the state of stress and anxiety.

The Beneficial Effects of the Invention

It is considered in traditional Chinese medicine that tumorigenesis usually results from external evil invasion, which could cause a functional disturbance in Yin and Yang, Qi and blood, channels and collaterals as well as the viscera and bowels. Therefore, the principle of cancer treatment in traditional Chinese medicine emphasizes regulating visceral function, consolidating the constitution and eliminating pathogenic factors. In recent years, Western medicine researchers have suggested that the main reason for tumorigenesis is that the immune function of patients was inhibited. So, increasing the immune function of the body and inhibiting the cancer cells are very important methods in the treatment of cancer.

Natural killer cells are provided by the immune system of the body. NK cells constitute a first line of defense against infectious disease and play a very important role in preventing the tumorigenesis and tumor metastases. The results of animal trials performed at the Immunology Lab of Tel-Aviv University of Israel demonstrated convincingly that NK cells played very important roles in controlling various aspects of tumor development, including the metastatic process, the tumorigenic effects of cancinogenes and the primary seeding of implanted solid tumors. ACNO can increase the number and activity of NK cells and inhibit the growth of tumors and prevent metastasis.

It has been suggested that *Scutellaria Baicalensis, Coptis Chinesis*, and *Phellodron Chinensis*, which are contained in the ACNO, are cytotoxic anti-cancer drugs; and Red Ginseng belongs to a class of chemoprophylactic agents of cancer. The resistance of anti-cancer drugs represents a major cause of failure in cancer chemotherapy, and to resolve this problem, extensive research was conducted and showed Red Ginseng is a new reversal agent with non-toxic effects.

Also, a series of tests were carried out to study the anti-cancer effects of ginsenoside Rg3. The pharmacological studies showed: (1) anti-tumor metastasis; (2) anti-cancer effects in that the inhibition rate of Rg3 against B16 melanoma, LEWIS lung cancer, and S180 sarcoma by subcutaneous transplantation were 50–60%; (3) Immunoenhancement effects since Rg3 administrated orally can remarkably enhance the NK and IL-2 activity of lung cancer implanted mice and normal mice; and (4) Rg3 can enhance the anti-cancer effect and reduce the side effects of chemotherapy. The studies on the mechanism of Rg3 showed that Rg3 can inhibit the proliferation, infiltration and metastasis of tumor cells, and enhance the immunological function of mice bearing tumors.

*Astragalus membranaceus, salvia miltiorrhiza* etc. possess the function of increasing the immunological function of organisms. The effective component of *Curcuma zedoaria* is cellular toxic, which inhibits the proliferation of tumor cells by inhibiting the protein synthetic processes of DNA and RNA, which might induce the termination of tumor cells' growth by way of blocking the cells' respiration in certain stages or destroying the cellular membrane to cause autolysis of the tumor cells. *Astragalus Membranaceus* combined with chemotherapy, radiotherapy and biological therapy may enhance the therapeutic effect and reduce the side effect thereof. The polysaccharide components of Radix Ginseng have reticuloendothelial system function-enhanced effect and contain trace amounts of Germanium (Ge), which has been known as an effective cancer-preventing element. The study of Ge in cancer prevention has vast prospects. The animal trials showed that ACNO can increase cytotoxic activity and the number of NK cells and suppress tumor metastasis. This result is consistent with that obtained from clinical trials and therefore is worthy of further research. ACNO and related treatment regimes using this composition, shall open a new avenue for preventing and treating cancer.

The anti-neoplastic compositions can increase immunity, inhibit tumor cells and reverse cells to a normal state; sedate the patient, and improve blood circulation in order to suppress the growth and metastasis of tumor; increase the sensitivity to radiotherapy and chemotherapy and reduce the toxic and adverse effects of radiotherapy and chemotherapy; improve sleeping, increase appetite, alleviate pain, and protect the function of the liver, kidney and ovaries; and increase the number of leukocyte and hemoglobin otherwise reduced by radiotherapy and chemotherapy. The compositions can also enhance the anti-tumor ability of the organism, prevent the relapse of tumors, improve the tumor patient's quality of life and prevent tumorigenesis.

The Chinese herbal medicines used in each prescription are available commercially in China. The various medicinal herbs were weighed according to the herbs employed and their percentage showed in the prescription, and then ground to powder, and encapsulated into capsules, 0.5 g per capsule.

The foregoing description is, at present, considered to be the preferred embodiments of the present invention. However, it is contemplated that various changes and modifications apparent to those skilled in the art, may be made without departing from the present invention. Therefore, the foregoing description is intended to cover all such changes and modifications encompassed within the spirit and scope of the present invention, including all equivalent aspects.

What is claimed is:

1. A composition for treatment of tumors, comprising effective amounts: Red Ren Shen (*PANAX GINSING*), Fu Ling (*PORIA COCOS*), Bai Zhu (*ATRACTYLODES MACROCEPHALA*), Huang Qi (*ASTRAGALUS MEMBRANACEUS*), Huang Qin (*SCUTELLARIA BAICALENSIS*), Huang Lian (*COPTIS CHINENSIS*), Gan Cao (*GLYCYRRHIZA URALENSIS*), Mai Ya (*HORDEUM VULGARE*), Bai Hua She She Cao (*HEDYOTIS DIFFUSA*), Ban Bian Lian (*LOBELIA CHINESIS LOUR*), Ban Zhi Lian (*SCUTELLARIA BARBABA*), Shen Qu (*MASSA FERMENTATA MEDICALIS*), and at least one agent selected from the group consisting of Dang Gui (*ANGELIC SINENSIS*), E Zhu (*CURCUMA ZEDOARIA*), Huang Bai (*PHELLODRON*

CHINENSE), Shan Zha (*CRATAEGUS PINATIFIDA*), Dan Shen (*SALVIA MILTIORRHIZA*), Wu Wei Zi (*SCHISANDRA CHINENSIS*), Mai Men Dong (*OPHIOPHOGON JAPONICUS*), Chai Hu (*BUPLEURUM SCORZONERIFOLIUM*), Ban Xia (*PINELLIA TERNATA*), Chen Pi (*CITRUS RETICULATA*), Chuan Lian Zi (*MELIA TOOSENDAN*), Bai Shao (*PAEONIA LACTIFLORA*), Ling Zhi (*GANODERMA LUCIDUM*), and Jiang (dry or fresh *ZINGIBER OFFICINALE*).

2. The composition for treatment of tumors according to claim 1, comprising:

| | | |
|---|---|---|
| about 9.4% | Red Ren Shen | (*PANAX GINSENG*); |
| about 5.7% | Fu Ling | (*PORIA COCOS*); |
| about 5.7% | Bai Zhu | (*ATRACTYLODES MACROCEPHALA*); |
| about 6.6% | Dang Gui | (*ANGELIC SINENSIS*) |
| about 5.7% | Huang Qi | (*ASTRAGALUS MEMBRANACEUS*); |
| about 4.7% | E Zhu | (*CURCUMA ZEDOARIA*); |
| about 5.7% | Huang Qin | (*SCUTELLARIA BAICALENSIS*); |
| about 4.7% | Huang Bai | (*PHELLODRON CHINENSE*); |
| about 5.7% | Huang Lian | (*COPTIS CHINENSIS*); |
| about 5.7% | Gan Cao | (*GLYCYRRHIZA URALENSIS*); |
| about 4.7% | Shan Zha | (*CRATAEGUS PINATIFIDA*); |
| about 1.8% | Mai Ya | (*HORDEUM VULGARE*); |
| about 4.7% | Dan Shen | (*SALVIA MILTIORRHIZA*); |
| about 5.7% | Wu Wei Zi | (*SCHISANDRA CHINENSIS*); |
| about 6.6% | Bai Hua She She Cao | (*HEDYOTIS DIFFUSA*); |
| about 4.7% | Mai Men Dong | (*OPHIOPHOGON JAPONICUS*); |
| about 4.7% | Ban Bian Lian | (*LOBELIA CHINESIS LOUR*); |
| about 5.7% | Ban Zhi Lian | (*SCUTELLARIA BARBABA*); |
| about 1.8% | Shen Qu | (*MASSA FERMENTATA MEDICALIS*). |

3. The composition for treatment of tumors according to claim 1, comprising:

| | | |
|---|---|---|
| about 1–15% | Red Ren Shen | (*PANAX GINSENG*); |
| about 1–10% | Fu Ling | (*PORIA COCOS*); |
| about 1–10% | Bai Zhu | (*ATRACTYLODES MACROCEPHALA*); |
| about 1–10% | Dang Gui | (*ANGELIC SINENSIS*); |
| about 1–10% | Huang Qi | (*ASTRAGALUS MEMBRANACEUS*); |
| about 1–10% | E Zhu | (*CURCUMA ZEDOARIA*); |
| about 1–25% | Huang Qin | (*SCUTELLARIA BAICALENSIS*); |
| about 1–20% | Huang Bai | (*PHELLODRON CHINENSE*); |
| about 1–20% | Huang Lian | (*COPTIS CHINENSIS*); |
| about 1–15% | Gan Cao | (*GLYCYRRHIZA URALENSIS*); |
| about 1–10% | Shan Zha | (*CRATAEGUS PINATIFIDA*); |
| about 1–20% | Mai Ya | (*HORDEUM VULGARE*); |
| about 1–15% | Dan Shen | (*SALVIA MILTIORRHIZA*); |
| about 1–15% | Wu Wei Zi | (*SCHISANDRA CHINENSIS*); |
| about 1–40% | Bai Hua She She Cao | (*HEDYOTIS DIFFUSA*); |
| about 1–20% | Mai Men Dong | (*OPHIOPHOGON JAPONICUS*); |
| about 1–25% | Ban Bian Lian | (*LOBELIA CHINESIS LOUR*); |
| about 1–25% | Ban Zhi Lian | (*SCUTELLARIA BARBABA*); |
| about 1–20% | Shen Qu | (*MASSA FERMENTATA MEDICALIS*). |

4. The composition for treatment of tumors according to claim 3, comprising:

| | | |
|---|---|---|
| about 9.4% | Red Ren Shen | (*PANAX GINSENG*); |
| about 5.7% | Fu Ling | (*PORIA COCOS*); |
| about 5.7% | Bai Zhu | (*ATRACTYLODES MACROCEPHALA*); |
| about 6.6% | Dang Gui | (*ANGELIC SINENSIS*); |
| about 5.7% | Huang Qi | (*ASTRAGALUS MEMBRANACEUS*); |
| about 4.7% | E Zhu | (*CURCUMA ZEDOARIA*); |
| about 5.7% | Huang Qin | (*SCUTELLARIA BAICALENSIS*); |
| about 4.7% | Huang Bai | (*PHELLODRON CHINENSE*); |
| about 5.7% | Huang Lian | (*COPTIS CHINENSIS*); |
| about 5.7% | Gan Cao | (*GLYCYRRHIZA URALENSIS*); |
| about 4.7% | Shan Zha | (*CRATAEGUS PINATIFIDA*); |
| about 1.8% | Mai Ya | (*HORDEUM VULGARE*); |
| about 4.7% | Dan Shen | (*SALVIA MILTIORRHIZA*); |
| about 5.7% | Wu Wei Zi | (*SCHISANDRA CHINENSIS*); |
| about 6.6% | Bai Hua She She Cao | (*HEDYOTIS DIFFUSA*); |
| about 4.7% | Mai Men Dong | (*OPHIOPHOGON JAPONICUS*); |
| about 4.7% | Ban Bian Lian | (*LOBELIA CHINESIS LOUR*); |
| about 5.7% | Ban Zhi Lian | (*SCUTELLARIA BARBABA*); |
| about 1.8% | Shen Qu | (*MASSA FERMENTATA MEDICALIS*). |

5. The composition for treatment of tumors according to claim 1, comprising:

| | | |
|---|---|---|
| about 1–30% | Red Ren Shen | (*PANAX GINSENG*); |
| about 1–30% | Fu Ling | (*PORIA COCOS*); |
| about 1–30% | Bai Zhu | (*ATRACTYLODES MACROCEPHALA*); |
| about 1–30% | Dang Gui | (*ANGELIC SINENSIS*); |
| about 1–30% | Huang Qi | (*ASTRAGALUS MEMBRANACEUS*); |
| about 1–30% | E Zhu | (*CURCUMA ZEDOARIA*); |
| about 1–35% | Huang Qin | (*SCUTELLARIA BAICALENSIS*); |
| about 1–30% | Huang Bai | (*PHELLODRON CHINENSE*); |
| about 1–30% | Huang Lian | (*COPTIS CHINENSIS*); |
| about 1–30% | Gan Cao | (*GLYCYRRHIZA URALENSIS*); |
| about 1–30% | Shan Zha | (*CRATAEGUS PINATIFIDA*); |
| about 1–30% | Mai Ya | (*HORDEUM VULGARE*); |
| about 1–30% | Dan Shen | (*SALVIA MILTIORRHIZA*); |
| about 1–30% | Wu Wei Zi | (*SCHISANDRA CHINENSIS*); |
| about 1–40% | Bai Hua She She Cao | (*HEDYOTIS DIFFUSA*); |
| about 1–30% | Mai Men Dong | (*OPHIOPHOGON JAPONICUS*); |
| about 1–35% | Ban Bian Lian | (*LOBELIA CHINESIS LOUR*); |
| about 1–35% | Ban Zhi Lian | (*SCUTELLARIA BARBABA*); |
| about 1–30% | Shen Qu | (*MASSA FERMENTATA MEDICALIS*). |

6. The composition for treatment of tumors according to claim 5, comprising:

| | | |
|---|---|---|
| about 9.4% | Red Ren Shen | (*PANAX GINSENG*); |
| about 5.7% | Fu Ling | (*PORIA COCOS*); |
| about 5.7% | Bai Zhu | (*ATRACTYLODES MACROCEPHALA*); |
| about 6.6% | Dang Gui | (*ANGELIC SINENSIS*); |
| about 5.7% | Huang Qi | (*ASTRAGALUS MEMBRANACEUS*); |
| about 4.7% | E Zhu | (*CURCUMA ZEDOARIA*); |
| about 5.7% | Huang Qin | (*SCUTELLARIA BAICALENSIS*); |
| about 4.7% | Huang Bai | (*PHELLODRON CHINENSE*); |
| about 5.7% | Huang Lian | (*COPTIS CHINENSIS*); |
| about 5.7% | Gan Cao | (*GLYCYRRHIZA URALENSIS*); |
| about 4.7% | Shan Zha | (*CRATAEGUS PINATIFIDA*); |
| about 1.8% | Mai Ya | (*HORDEUM VULGARE*); |
| about 4.7% | Dan Shen | (*SALVIA MILTIORRHIZA*); |
| about 5.7% | Wu Wei Zi | (*SCHISANDRA CHINENSIS*); |
| about 6.6% | Bai Hua She She Cao | (*HEDYOTIS DIFFUSA*); |
| about 4.7% | Mai Men Dong | (*OPHIOPHOGON JAPONICUS*); |
| about 4.7% | Ban Bian Lian | (*LOBELIA CHINESIS LOUR*); |
| about 5.7% | Ban Zhi Lian | (*SCUTELLARIA BARBABA*); |
| about 1.8% | Shen Qu | (*MASSA FERMENTATA MEDICALIS*). |

7. The composition for treatment of tumors according to claim 1, comprising:

| | | |
|---|---|---|
| about 1–30% | Red Ren Shen | (*PANAX GINSENG*); |
| about 1–30% | Fu Ling | (*PORIA COCOS*); |
| about 1–30% | Bai Zhu | (*ATRACTYLODES MACROCEPHALA*); |
| about 1–30% | Dang Gui | (*ANGELIC SINENSIS*); |

-continued

| | | |
|---|---|---|
| about 1–30% | Huang Qi | (*ASTRAGALUS MEMBRANACEUS*); |
| about 1–30% | Huang Qin | (*SCUTELLARIA BAICALENSIS*); |
| about 1–30% | Huang Lian | (*COPTIS CHINENSIS*); |
| about 1–30% | Huang Bai | (*PHELLODRON CHINENSE*); |
| about 1–30% | Gan Cao | (*GLYCYRRHIZA URALENSIS*); |
| about 1–30% | Mai Ya | (*HORDEUM VULGARE*); |
| about 1–40% | Bai Hua She She Cao | (*HEDYOTIS DIFFUSA*); |
| about 1–30% | Ban Bian Lian | (*LOBELIA CHINESIS LOUR*); |
| about 1–30% | Ban Zhi Lian | (*SCUTELLARIA BARBABA*); |
| about 1–30% | Shen Qu | (*MASSA FERMENTATA MEDICALIS*); |
| about 1–30% | Chai Hu | (*BUPLEURUM SCORZONERIFOLIUM*); |
| about 1–30% | Ban Xia | (*PINELLIA TERNATA*); |
| about 1–30% | Chen Pi | (*CITRUS RETICULATA*); |
| about 1–30% | Chuan Lian Zi | (*MELIA TOOSENDAN*); |
| about 1–30% | Bai Shao | (*PAEONIA LACTIFLORA*); and |
| about 1–30% | Jiang (GAN or SHENG) | (*ZINGIBER OFFICINALE*) (dry or fresh). |

8. The composition for treatment of tumors according to claim 7, comprising:

| | | |
|---|---|---|
| about 9.4% | Red Ren Shen | (*PANAX GINSENG*); |
| about 5.7% | Fu Ling | (*PORIA COCOS*); |
| about 5.7% | Bai Zhu | (*ATRACTYLODES MACROCEPHALA*); |
| about 6.6% | Dang Gui | (*ANGELIC SINENSIS*); |
| about 5.7% | Huang Qi | (*ASTRAGALUS MEMBRANACEUS*); |
| about 5.7% | Huang Qin | (*SCUTELLARIA BAICALENSIS*); |
| about 5.7% | Huang Lian | (*COPTIS CHINENSIS*); |
| about 4.7% | Huang Bai | (*PHELLODRON CHINENSE*); |
| about 5.7% | Gan Cao | (*GLYCYRRHIZA URALENSIS*); |
| about 1.8% | Mai Ya | (*HORDEUM VULGARE*); |
| about 6.6% | Bai Hua She She Cao | (*HEDYOTIS DIFFUSA*); |
| about 4.7% | Ban Bian Lian | (*LOBELIA CHINESIS LOUR*); |
| about 5.7% | Ban Zhi Lian | (*SCUTELLARIA BARBABA*); |
| about 1.8% | Shen Qu | (*MASSA FERMENTATA MEDICALIS*); |
| about 5.0% | Chai Hu | (*BUPLEURUM SCORZONERIFOLIUM*) |
| about 5.0% | Ban Xia | (*PINELLIA TERNATA*); |
| about 5.0% | Chen Pi | (*CITRUS RETICULATA*); |
| about 5.0% | Chuan Lian Zi | (*MELIA TOOSENDAN*); |
| about 4.0% | Bai Shao | (*PAEONIA LACTIFLORA*); and |
| about 2.0% | Jiang (GAN or SHENG) | (*ZINGIBER OFFICINALE*) (dry or fresh). |

9. The composition for treatment of tumors according to claim 1, comprising:

| | | |
|---|---|---|
| about 1–30% | Red Ren Shen | (*PANAX GINSENG*); |
| about 1–30% | Fu Ling | (*PORIA COCOS*); |
| about 1–30% | Bai Zhu | (*ATRACTYLODES MACROCEPHALA*); |
| about 1–30% | Dang Gui | (*ANGELIC SINENSIS*); |
| about 1–30% | Huang Qi | (*ASTRAGALUS MEMBRANACEUS*); |
| about 1–30% | Huang Qin | (*SCUTELLARIA BAICALENSIS*); |
| about 1–30% | Huang Lian | (*COPTIS CHINENSIS*); |
| about 1–30% | Gan Cao | (*GLYCYRRHIZA URALENSIS*); |
| about 1–30% | Mai Ya | (*HORDEUM VULGARE*); |
| about 1–40% | Bai Hua She She Cao | (*HEDYOTIS DIFFUSA*); |
| about 1–30% | Ban Bian Lian | (*LOBELIA CHINESIS LOUR*); |
| about 1–30% | Ban Zhi Lian | (*SCUTELLARIA BARBABA*); |
| about 1–30% | Shen Qu | (*MASSA FERMENTATA MEDICALIS*); |
| about 1–30% | Chai Hu | (*BUPLEURUM SCORZONERIFOLIUM*); |
| about 1–30% | Ban Xia | (*PINELLIA TERNATA*); |
| about 1–30% | Chen Pi | (*CITRUS RETICULATA*); |
| about 1–30% | Chuan Lian Zi | (*MELIA TOOSENDAN*); |
| about 1–30% | Bai Shao | (*PAEONIA LACTIFLORA*). |

10. The composition of claim 9 further comprising:

| | | |
|---|---|---|
| about 1–30% | Huang Bai | (*PHELLODRON CHINENSE*). |

11. The composition of claim 9 further comprising:

| | | |
|---|---|---|
| about 1–30% | Jiang (dry or fresh) | (*ZINGIBER OFFICINALE*). |

12. The composition for treatment of tumors according to claim 9, comprising:

| | | |
|---|---|---|
| about 9.4% | Red Ren Shen | (*PANAX GINSENG*); |
| about 5.7% | Fu Ling | (*PORIA COCOS*); |
| about 5.7% | Bai Zhu | (*ATRACTYLODES MACROCEPHALA*); |
| about 6.6% | Dang Gui | (*ANGELIC SINENSIS*); |
| about 5.7% | Huang Qi | (*ASTRAGALUS MEMBRANACEUS*); |
| about 5.7% | Huang Qin | (*SCUTELLARIA BAICALENSIS*); |
| about 5.7% | Huang Lian | (*COPTIS CHINENSIS*); |
| about 5.7% | Gan Cao | (*GLYCYRRHIZA URALENSIS*); |
| about 1.8% | Mai Ya | (*HORDEUM VULGARE*); |
| about 6.6% | Bai Hua She She Cao | (*HEDYOTIS DIFFUSA*); |
| about 4.7% | Ban Bian Lian | (*LOBELIA CHINESIS LOUR*); |
| about 5.7% | Ban Zhi Lian | (*SCUTELLARIA BARBABA*); |
| about 1.8% | Shen Qu | (*MASSA FERMENTATA MEDICALIS*); |
| about 5.0% | Chai Hu | (*BUPLEURUM SCORZONERIFOLIUM*) |
| about 5.0% | Ban Xia | (*PINELLIA TERNATA*); |
| about 5.0% | Chen Pi | (*CITRUS RETICULATA*); |
| about 5.0% | Chuan Lian Zi | (*MELIA TOOSENDAN*); |
| about 4.0% | Bai Shao | (*PAEONIA LACTIFLORA*). |

13. The composition of claim 12 further comprising:

| | | |
|---|---|---|
| about 4.7% | Huang Bai | (*PHELLODRON CHINENSE*). |

14. The composition of claim 12 further comprising:

| | | |
|---|---|---|
| about 2.0% | Jiang(dry or fresh) | (*ZINGIBER OFFICINALE*). |

15. The composition for treatment of tumors according to claim 1, comprising:

| | | |
|---|---|---|
| about 1–30% | Red Ren Shen | (*PANAX GINSENG*); |
| about 1–30% | Fu Ling | (*PORIA COCOS*). |
| about 1–30% | Bai Zhu | (*ATRACTYLODES MACROCEPHALA*); |
| about 1–30% | Dang Gui | (*ANGELIC SINENSIS*); |
| about 1–30% | Huang Qi | (*ASTRAGALUS MEMBRANACEUS*); |
| about 1–30% | Huang Qin | (*SCUTELLARIA BAICALENSIS*); |
| about 1–30% | Huang Lian | (*COPTIS CHINENSIS*); |
| about 1–30% | Gan Cao | (*GLYCYRRHIZA URALENSIS*); |
| about 1–30% | Mai Ya | (*HORDEUM VULGARE*); |
| about 1–40% | Bai Hua She She Cao | (*HEDYOTIS DIFFUSA*); |
| about 1–30% | Ban Bian Lian | (*LOBELIA CHINESIS LOUR*); |
| about 1–30% | Ban Zhi Lian | (*SCUTELLARIA BARBABA*); |
| about 1–30% | Shen Qu | (*MASSA FERMENTATA MEDICALIS*); |
| about 1–30% | Chai Hu | (*BUPLEURUM SCORZONERIFOLIUM*) |
| about 1–30% | Ban Xia | (*PINELLIA TERNATA*); |
| about 1–30% | Chen Pi | (*CITRUS RETICULATA*); |

| | | |
|---|---|---|
| about 1–30% | Chuan Lian Zi | (*MELIA TOOSENDAN*); |
| about 1–30% | Bai Shao | (*PAEONIA LACTIFLORA*); and |
| about 1–30% | Ling Zhi | (*GANODERMA LUCIDUM*). |

16. The composition of claim 15 further comprising:

| | | |
|---|---|---|
| about 1–30% | Huang Bai (PHELLODRON CHINENSE). | |

17. The composition of claim 15 further comprising:

| | | |
|---|---|---|
| about 1–30% | Jiang (GAN or SHENG) (ZINGIBER OFFICINALE) (dry or fresh). | |

18. The composition for treatment of tumors according to claim 15, comprising:

| | | |
|---|---|---|
| about 9.4% | Red Ren Shen | (PANAX GINSING); |
| about 5.7% | Fu Ling | (PORIA COCOS); |
| about 5.7% | Bal Zhu | (ATRACTYLODES MACROCEPHALA); |
| about 6.6% | Dang Gui | (ANGELIC SINENSIS); |
| about 5.7% | Huang Qi | (ASTRAGALUS MEMBRANACEUS); |
| about 5.7% | Huang Qin | (SCUTELLARIA BAICALENSIS); |
| about 5.7% | Huang Lian | (COPTIS CHINENSIS); |
| about 5.7% | Gan Cao | (GLYCYRRHIZA URALENSIS); |
| about 1.8% | Mai Ya | (HORDEUM VULGARE); |
| about 6.6% | Bai Hua She She Cao | (HEDYOTIS DIFFUSA); |
| about 4.7% | Ban Bian Lian | (LOBELIA CHINESIS LOUR); |
| about 5.7% | Ban Zhi Lian | (SCUTELLARIA BARBABA); |
| about 1.8% | Shen Qu | (MASSA FERMENTATA MEDICALIS); |
| about 5.0% | Chai Hu | (BUPLEURUM SCORZONERIFOLIUM) |
| about 5.0% | Ban Xia | (PINELLIA TERNATA); |
| about 5.0% | Chen Pi | (CITRUS RETICULATA); |
| about 5.0% | Chuan Lian Zi | (MELIA TOOSENDAN); |
| about 4.0% | Bai Shao | (PAEONIA LACTIFLORA); and |
| about 6.0% | Ling Zhi | (GANODERMA LUCIDUM). |

19. The composition of claim 18 further comprising:

| | | |
|---|---|---|
| about 4.7% | Huang Bai (PHELLODRON CHINENSE). | |

20. The composition of claim 18 further comprising:

| | | |
|---|---|---|
| about 2.0% | Jiang (dry or fresh) (ZINGIBER OFFICINALE). | |

* * * * *

UNITED STATES PATENT AND TRADEMARK OFFICE
CERTIFICATE OF CORRECTION

PATENT NO. : 6,911,221 B2
DATED : June 28, 2005
INVENTOR(S) : Hongfen Li It is certified that error appears in the above-identified patent and that said Letters Patent is hereby corrected as shown below:

<u>Title page,</u>
Insert Item: -- [30] Foreign Application Priority Data
                ISRAEL 135325  04/02/2001 --.

Signed and Sealed this

Thirtieth Day of August, 2005

JON W. DUDAS
*Director of the United States Patent and Trademark Office*